(12) United States Patent
Acuna et al.

(10) Patent No.: US 11,751,843 B2
(45) Date of Patent: Sep. 12, 2023

(54) ULTRASOUND TRANSDUCER HOLDER FOR VASCULAR ASSESSMENTS DURING HYPEREMIC BLOOD FLOW

(71) Applicant: Board of Regents, The University of Texas System, Austin, TX (US)

(72) Inventors: Francisco Morales Acuna, El Paso, TX (US); Luis A. Ochoa, El Paso, TX (US); Alvaro N. Gurovich, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 584 days.

(21) Appl. No.: 16/591,798

(22) Filed: Oct. 3, 2019

(65) Prior Publication Data
US 2020/0155117 A1 May 21, 2020

Related U.S. Application Data

(60) Provisional application No. 62/768,794, filed on Nov. 16, 2018.

(51) Int. Cl.
*A61B 8/00* (2006.01)
*A61B 8/06* (2006.01)

(52) U.S. Cl.
CPC .......... *A61B 8/4209* (2013.01); *A61B 8/06* (2013.01); *A61B 8/4455* (2013.01); *A61B 8/4461* (2013.01); *A61B 8/4483* (2013.01)

(58) Field of Classification Search
CPC ....... A61B 8/4209; A61B 8/06; A61B 8/4455; A61B 8/4483; A61B 8/4461; A61B 8/4227
See application file for complete search history.

(56) References Cited

U.S. PATENT DOCUMENTS

| | | | | |
|---|---|---|---|---|
| 4,920,966 A | * | 5/1990 | Hon | A61B 5/4356 600/459 |
| 5,381,794 A | * | 1/1995 | Tei | A61B 8/4281 600/459 |
| 2008/0064960 A1 | * | 3/2008 | Whitmore, III | A61B 8/4218 600/459 |
| 2018/0263597 A1 | * | 9/2018 | Tchang | G10K 11/352 |

* cited by examiner

*Primary Examiner* — Boniface Ngathi
*Assistant Examiner* — Zainab Mohammed Aldarraji
(74) *Attorney, Agent, or Firm* — Yee & Associates, P.C.

(57) ABSTRACT

An ultrasound transducer probe holder device comprising a support piece; a base connected to the support piece; a cylindrical orifice within the support piece; a housing extending from the orifice and defining a cavity; a sleeve for insertion within the orifice; and an adjustment screw fitted in the housing for contact with the sleeve. The device supports and maintains the position of an ultrasound transducer probe to provide for a hands-free application of the device during different modalities of exercise required to instigate hyperemic conditions while providing x, y, z, positional adjustments of the probe relative to the patient.

20 Claims, 13 Drawing Sheets

ULTRASOUND TRANSDUCER HOLDER FOR VASCULAR ASSESSMENTS DURING HYPEREMIC BLOOD FLOW

CROSS-REFERENCE TO RELATED APPLICATION(S)

This application claims the benefit of priority to U.S. Provisional Patent Application No. 62/768,794, filed Nov. 16, 2018, the entire contents of which are incorporated herein by reference.

BACKGROUND INFORMATION

1. Field

The present disclosure relates to ultrasound imaging and more particular to methods and devices for positioning ultrasound transducers for vascular assessments during hyperemic conditions.

2. Background

The first step of the development of cardiovascular diseases is a process known as endothelial dysfunction (ED) in which the inner layer of the arteries is unable to generate several biochemical protective molecules necessary to maintain homeostasis. Flow mediated dilation (FMD) is a clinical, noninvasive way to test for ED. FMD uses ultrasound imaging of the brachial, popliteal, and femoral arteries to test their dilatory capacity in response to hyperemic flow after a 5-minute occlusion period.

Although FMD has been used in research for more than 20 years showing significant results relevant to vascular physiology, it has not been able to translate its performance to the doctor office. More current studies involving vascular health are employing ultrasound imaging of the brachial and carotid arteries to assess the behavior of blood flow during exercise, but they have found many difficulties in the image acquisition.

To date, vascular assessments using ultrasound imaging, such as FMD, are operator dependent because a trained sonographist must hold the transducer probe of the ultrasound in the same position on the patient continuously for approximately ten minutes. This task is difficult to accomplish because the hand of the operator may fatigue causing movement of the probe and affecting the measurements. Maintaining the position of the probe is further complicated by movement of the patient during the different modalities of exercise in order to instigate hyperemic conditions required for the test.

SUMMARY

An example ultrasound transducer probe holder device includes a trunk section with an orifice in communication with a channel within the trunk section, a base connected to the trunk section, a sleeve removably located within the channel, and an adjustment screw fitted in the housing, wherein the adjustment screw is movable into the channel to secure the sleeve to the trunk section.

An example method of securing an ultrasound transducer probe holder device to a patient includes inserting an ultrasound transducer probe through an orifice in communication with a channel within a support piece, inserting the ultrasound transducer probe into a sleeve, inserting the sleeve with the ultrasound transducer probe into the support piece, securing the sleeve to the support piece, and securing the support piece to the patient.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
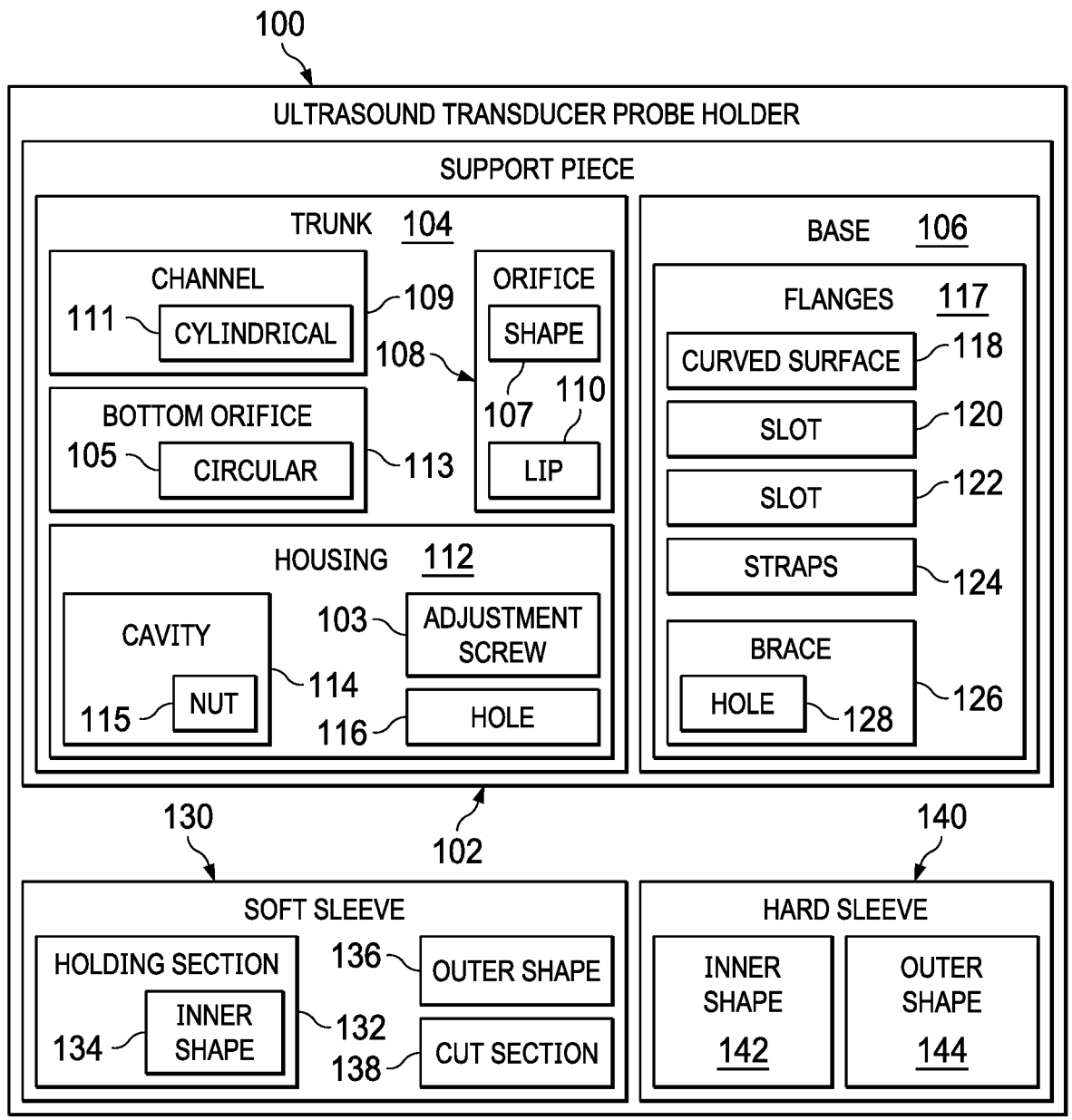
FIG. 1 is an illustration of a block diagram of an ultrasound transducer probe holder device in accordance with an illustrative embodiment.

The illustrative embodiments disclose an ultrasound transducer probe holder device that assists with vascular assessments via ultrasound imaging. The device allows practitioners to use FMD testing in the brachial, femoral, popliteal, or carotid arteries to assess blood flow patterns and velocities as well as arterial diameters during exercise conditions while decreasing the variability of the vascular imaging. No external human manipulation is needed during the imaging procedure once the device is properly positioned. The device improves the accuracy and reproducibility of non-invasive clinical tests to detect cardiovascular diseases through ultrasound imaging.

The device is proportioned in accordance with the specifications of commercially-available ultrasound transducers. The device may be created using a digital and 3D printer process. The device is adjustable to their respective surface (e.g. arm, leg, and neck). The device supports the transducer probe of ultrasound components to provide for a hands-free application of ultrasound imaging with x, y, z, and angular adjustments for location and pressure on the patient. The device can maintain the image even during limb motion so it can be used to assess the vasculature during different modalities of exercise (e.g. running, strength training, boxing training, cycling, arm-cranking).

To date, vascular assessments using ultrasound imaging, such as FMD, are operator dependent because a trained sonographist must hold the probe of the ultrasound in the same position on the patient continuously for at least 10 minutes. This task is difficult to accomplish because the hand of the operator will fatigue after a couple of minutes and will affect the measurements. Also, there is some risk of tendinopathies on the sonographer if the procedure is repeated too many times during a period. An alternative method for collecting FMD images is attaching the transducer probe to an external stereotaxic arm. However, if the patient moves, the image will be lost and the sonographist still must maintain a hand on the probe continuously to ensure a good quality image. With the disclosed device there is no need of external human manipulation during the procedure once the device is correctly located, avoiding the error of measurement and preventing any kind of injury to the sonographist for the extended data taking cycle. The device is attached to the patient's arm, leg, or neck, so even if the patient moves, the image is not lost, and there is no need to restart the test procedure.

The device is designed to improve the acquisition of images during vascular assessments with ultrasound imaging during hyperemic conditions, such as FMD and exercise, without external human manipulation, allowing for a more comfortable and reliable testing procedure. Additionally, the shape of the device allows the sonographist to easily adjust the position and orientation of the probe before starting any measurements. The device is form fitting, and so it is comfortable for the patient and allows for some minor movement of the patient during the data taking process. Further, previous studies involving the assessment of the vasculature during exercise have been limited only to cycling activities and as mentioned before, the device can be employed in a wide variety of activities.

The device was tested during FMD in 26 healthy young subjects. The coefficient of variation for baseline artery diameter, peak artery diameter, % FMD, and delta-FMD were 0.26±0.39%, 0.40±0.42%, 6.44±6.1%, and 6.27±6.09%, respectively. The results (Attached as Appendix A) show an excellent reliability for the use of the device for FMD. The device was also employed in the analysis of blood flow patterns of the carotid and brachial artery during exercise at different intensities. The device was comfortable for the subjects and clear ultrasound images of the vessels throughout the exercise bouts was obtained.

With reference to FIG. 1, an illustration of a block diagram of an ultrasound transducer probe holder device is depicted in accordance with an illustrative embodiment. In the illustrative examples, the same reference numeral may be used in more than one figure. This reuse of a reference numeral in different figures represents the same element in the different figures.

In the illustrative example, ultrasound transducer probe holder 100 may be comprised of support piece 102, soft sleeve 130, and hard sleeve 140.

Support piece 102 may be comprised of trunk 104 and base 106. Trunk 104 may be unitarily formed with base 106. Trunk 104 may be connected to base 106.

Trunk 104 may include orifice 108. Orifice 108 may have a 2D shape 107 that mimics the shape of the transducer probe to allow probe insertion. Orifice may include lip 110. Orifice 108 leads to channel 109 of trunk 104. Channel 109 may have cylindrical shape 111. Channel 109 passes through trunk 104 and base 106. Channel 109 may include bottom orifice 113. Bottom orifice 113 may be circular 105 shaped. Trunk 104 may include housing 112. Housing 112 may define cavity 114 sized to accept nut 115. Housing may include hole 116 sized to engage adjustment screw 103.

Base 106 may include flanges 117. Flanges may have curved surface 118. Flanges may further include slots 120, 122 for accommodation of attachment straps 124. Support piece may be secured to flexible brace 126 with trunk 104 extending through hole 128 in brace 126 such that flanges 117 and housing 112 abuts brace 126 on opposite sides of hole 128.

Soft sleeve 130 may comprise holding section 132. Holding section 132 is a channel through soft sleeve 130 that may have inner shape 134 shaped to accommodate an ultrasound transducer probe. Soft sleeve 130 may include a generally round outer shape 136. Soft sleeve 130 may include cut section 138 which allows soft sleeve 130 to be opened in order to accommodate insertion of an ultrasound transducer probe within holding section 132.

Hard sleeve 140 may comprise inner shape 142 shaped to accommodate soft sleeve 130. Inner shape 142 mimics outer shape 136 of soft sleeve 130. Hard sleeve 140 may include a generally round outer shape 144. Outer shape 144 is sized to be fitted within channel 109 of support piece 102.

Figure 2:
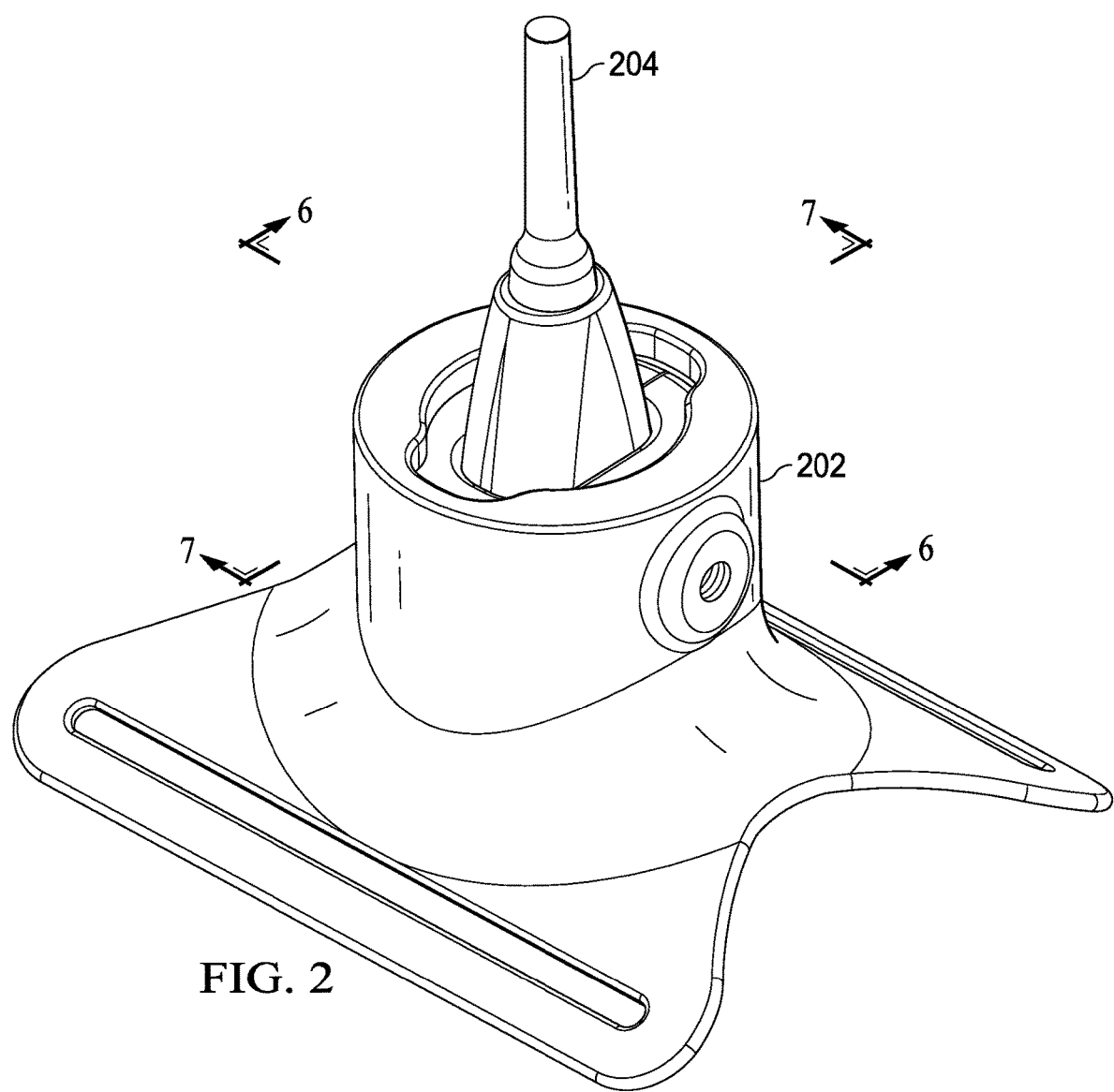
FIG. 2 illustrates an ultrasound transducer probe holder device in use, in accordance with an illustrative embodiment.

FIG. 2 illustrates an ultrasound transducer probe holder device with an ultrasound transducer probe, in accordance with an illustrative embodiment. Ultrasound transducer probe holder 202 is an example of one implementation of ultrasound transducer probe holder 100 in FIG. 1. Ultrasound transducer probe holder 202 may position ultrasound transducer probe 204 against the arm, leg, or neck of a patient to provide hands-free operation of FMD testing on a subject during exercise conditions. Ultrasound transducer probe holder 202 may include a support piece, a hard sleeve, and a soft sleeve. The support piece and the hard sleeve may comprise a shore D material plastic, for example, polycarbonate material crafted with 3D printing. The soft sleeve may comprise a shore A material, for example, a silicone or urethane material and manufactured through room temperature vulcanization molding.

Figure 3:
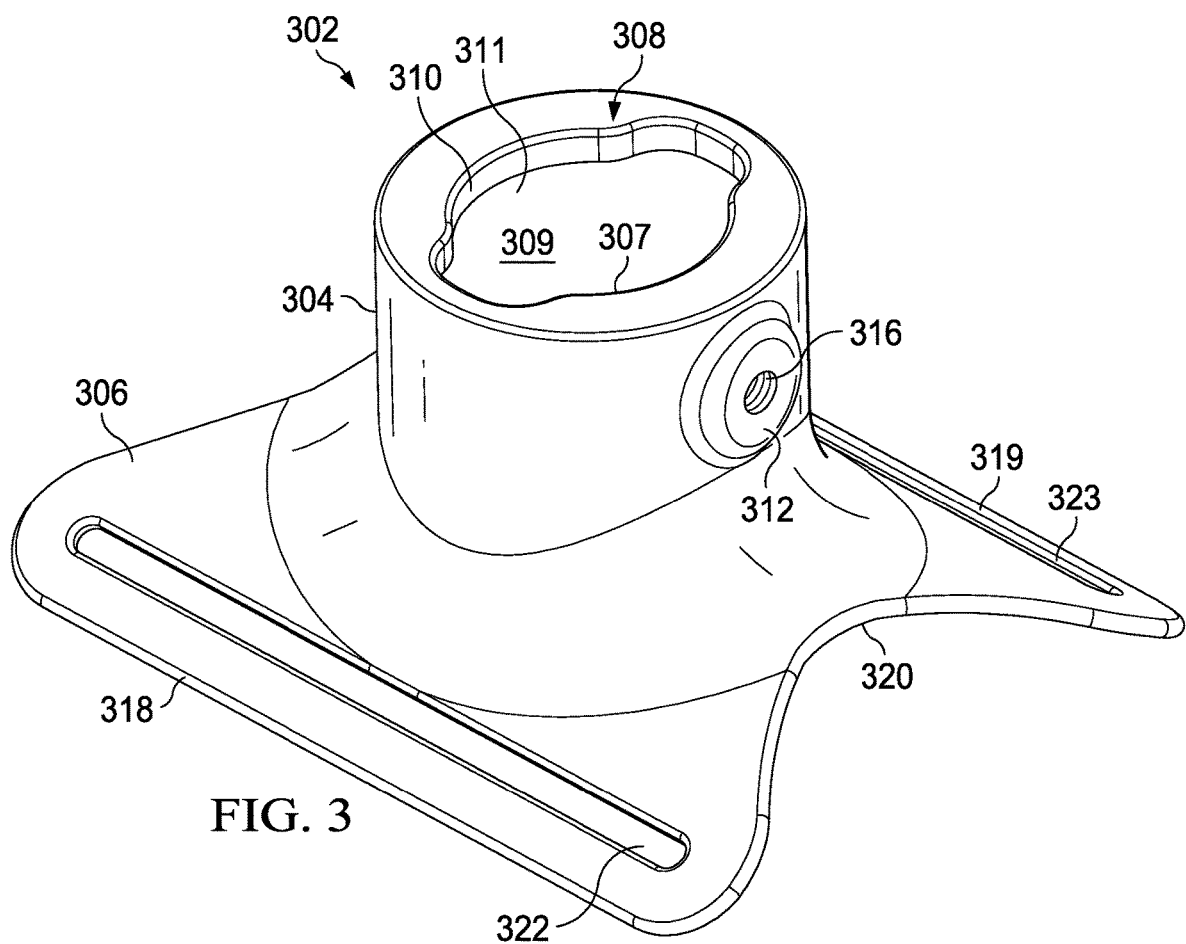
FIG. 3 illustrates a support piece, in accordance with an illustrative embodiment.

FIG. 3 illustrates support piece 302 of ultrasound transducer probe holder 202 in accordance with an illustrative embodiment. Support piece 302 is an example of one implementation of support piece 102 in FIG. 1. Support piece 302 may include trunk section 304 and base 306. Trunk section 304 and base 306 may be of unitary construction. Trunk section 304 may be connected to base 306.

Trunk section 304 may include orifice 308 leading to channel 309. Channel 309 extends through trunk section 304 and base 306. Channel 309 may have cylindrical shape 311. Channel 309 may include orifice 308 with a 2D shape 307 of the transducer probe to allow probe insertion, and a bottom round orifice (shown as bottom orifice 608 of FIG. 6) to allow insertion of the sleeves. Orifice 308 of trunk section 304 may include lip 310. Lip 310 may contact the hard sleeve (shown as hard sleeve 502 of FIG. 5) and the soft sleeve (shown as soft sleeve 402 of FIG. 4) when the sleeves are positioned within channel 309 of support piece 302 to prevent the sleeves from exiting the support piece 302 through orifice 308. Trunk section 304 may include housing 312. Housing 312 defines threaded hole 316 sized to accommodate an adjustment screw. Threaded hole 316 leads to channel 309. An adjustment screw in threaded hole 316 may contact the hard sleeve when the hard and soft sleeves are both positioned within channel 309 of support piece 302. The adjustment screw is used to fix the position of the sleeves relative to support piece 302. It is possible to operate ultrasound transducer probe holder 202 with both the hard sleeve and the soft sleeve in conjunction within the support piece 302. It is also possible to operate ultrasound transducer probe holder 202 with the hard sleeve absent. When the hard sleeve is absent, the adjustment screw contacts the soft sleeve to secure the position of the soft sleeve relative to support piece 302. With the hard sleeve in place, the hard sleeve prolongs the life of the soft sleeve after repeated tightening and loosening of the adjustment screw.

Base 306 may include flanges 318, 319 extending from trunk section 304. Flanges 318, 319 of base 306 may form curved surface 320. Curved surface 320 is shaped to contact a subject for a comfortable and secure placement on an appendage or neck of a patient. Flanges 318, 319 may include slots 322, 323 for accommodating straps having a hook and loop fastener arrangement for securing ultrasound transducer probe holder 202 to a patient. The straps allow for adjustment to accommodate various sizes of patient appendages.

Figure 4:
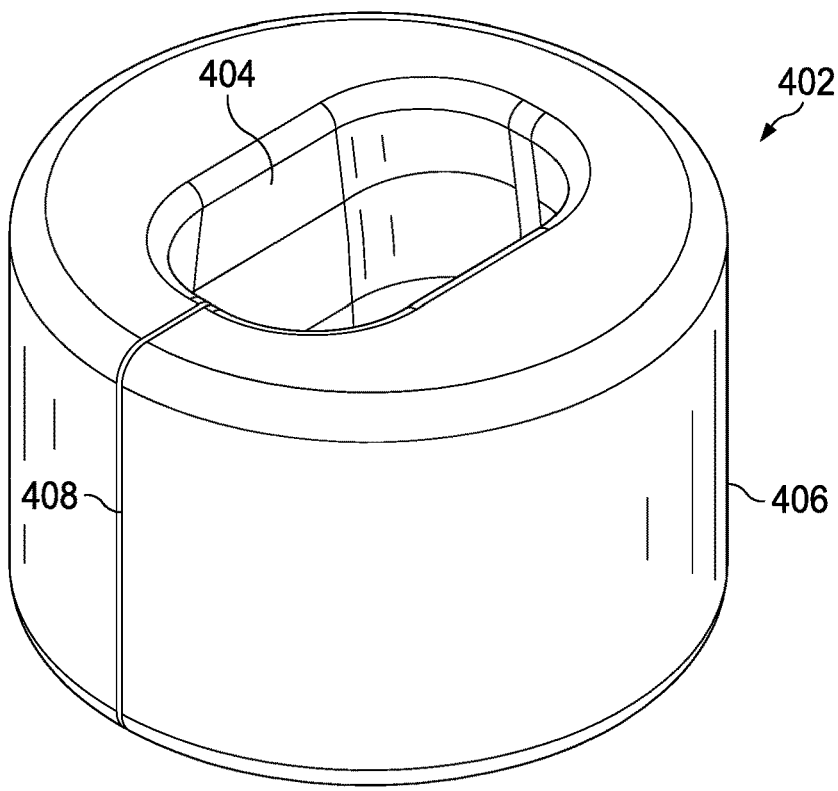
FIG. 4 illustrates a soft sleeve, in accordance with an illustrative embodiment.

FIG. 4 illustrates soft sleeve 402 of ultrasound transducer probe holder 202 in accordance with an illustrative embodiment. Soft sleeve 402 is an example of one implementation of soft sleeve 130 in FIG. 1. Soft Sleeve 402 may include holding section 404. Holding section 404 is a channel through soft sleeve 402 that is shaped to snugly accommodate an ultrasound transducer probe. Soft sleeve 402 may include a generally round outer shape 406. Outer shape 406 is sized to be fitted within hard sleeve 502, that at the same time is to be fitted within channel 309 of support piece 302. Soft sleeve 402 may include cut section 408. Cut section 408 extends through to holding section 404 and allows soft sleeve 402 to be opened in order to accommodate insertion of an ultrasound transducer probe within holding section 404.

Figure 5:
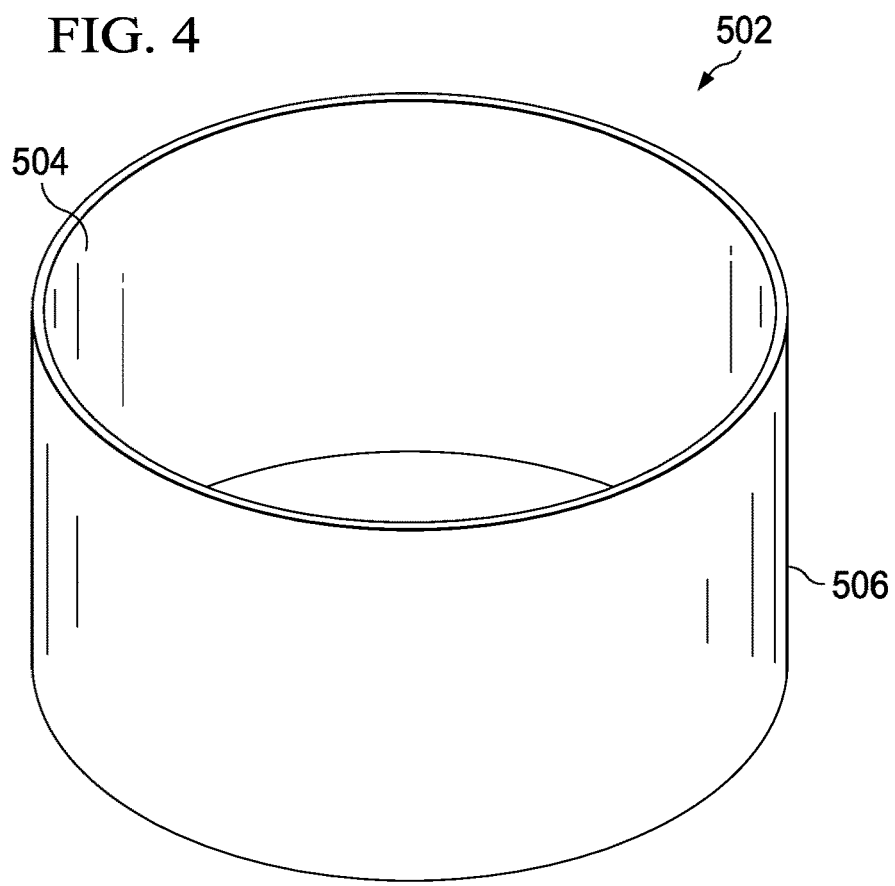
FIG. 5 illustrates a hard sleeve, in accordance with an illustrative embodiment.

FIG. 5 illustrates hard sleeve 502 of ultrasound transducer probe holder 202 in accordance with an illustrative embodiment. Hard sleeve 502 is an example of one implementation of hard sleeve 140 in FIG. 1. Hard Sleeve 502 has inner shape 504 shaped to accommodate soft sleeve 402. Inner shape 504 of hard sleeve 502 mimics outer shape 406 of soft sleeve 402. Hard sleeve 502 may include a generally round outer shape 506. Outer shape 506 is sized to be fitted within channel 309 of support piece 302. Outer shape 506 allows rotation of hard sleeve 502, and thus soft sleeve 402 within, with respect to support piece 302 for positioning and visualization of an ultrasound transducer probe.

Figure 6:
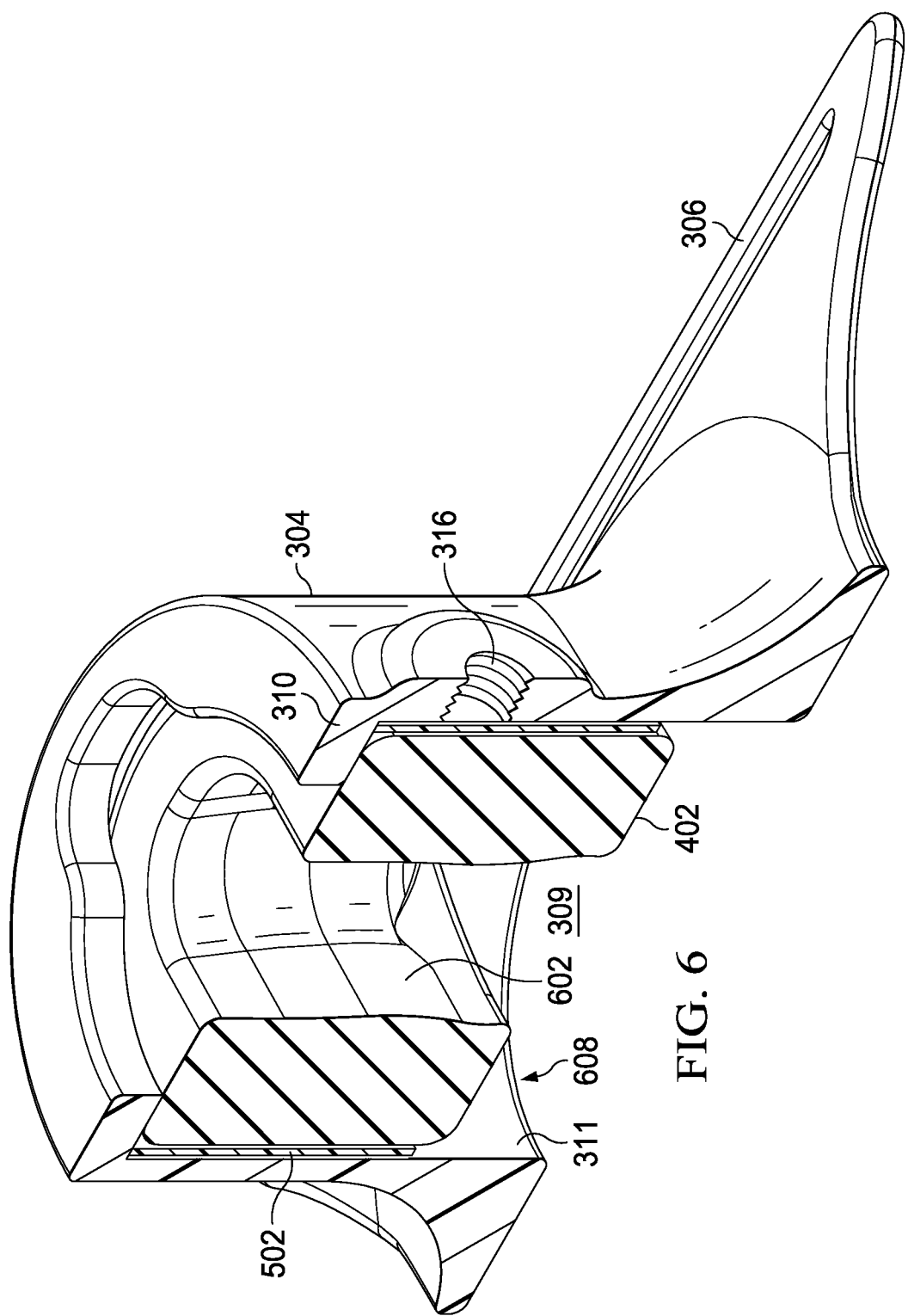
FIGS. 6-7 illustrate an ultrasound transducer probe holder device in use in cross section taken along lines 6-6 and 7-7 of FIG. 2, in accordance with an illustrative embodiment.
Figure 7:
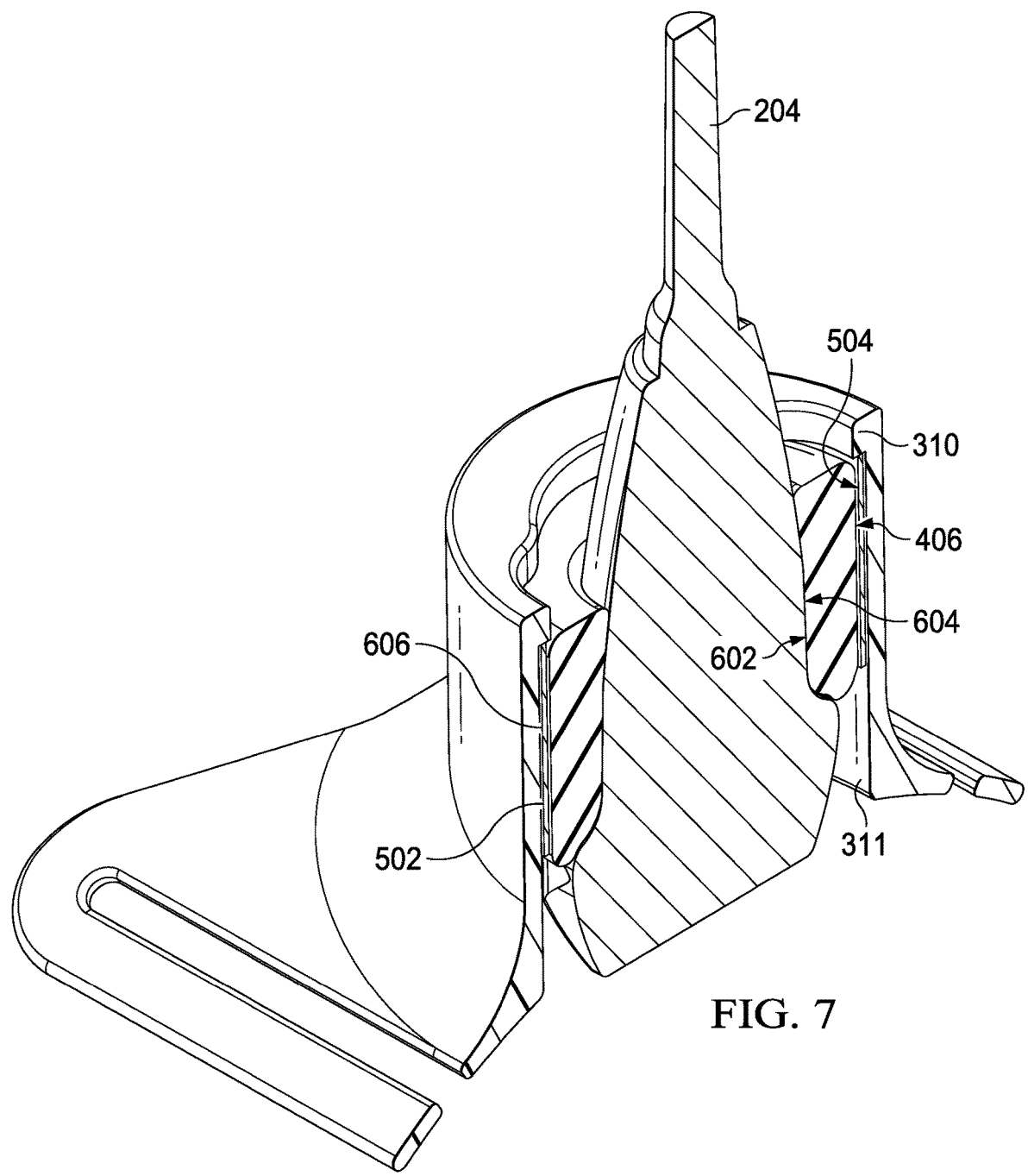

As best illustrated in FIGS. 6-7, inner shape 602 of soft sleeve 402 mimics outer shape 604 of ultrasound transducer probe 204, allowing better holding of and avoiding movement of the transducer probe during testing. Outer shape 606 of hard sleeve 502 allows hard sleeve 502 to be inserted in to channel 309 through bottom orifice 608 and rotate within channel 309 of support piece 302. Bottom orifice 608 is circular in shape. Outer shape 606 of hard sleeve 502 mimics inner cylindrical shape 311 of channel 309 and the circular shape of bottom orifice 608. The shore A material selected for soft sleeve 402 allows certain angular and x, y, z movements of ultrasound transducer probe 204 for final adjustment relative to the patient. The shore A material selected also provides certain compression that helps ultrasound transducer probe 204 to be touching, tight and secured to a patient appendage, allowing a better visualization of blood flow.

Lip 310 prevents soft sleeve 402 and hard sleeve 502 and thus ultrasound transducer probe 204 held within soft sleeve 402 from exiting support piece 302 through orifice 308.

Figure 8:
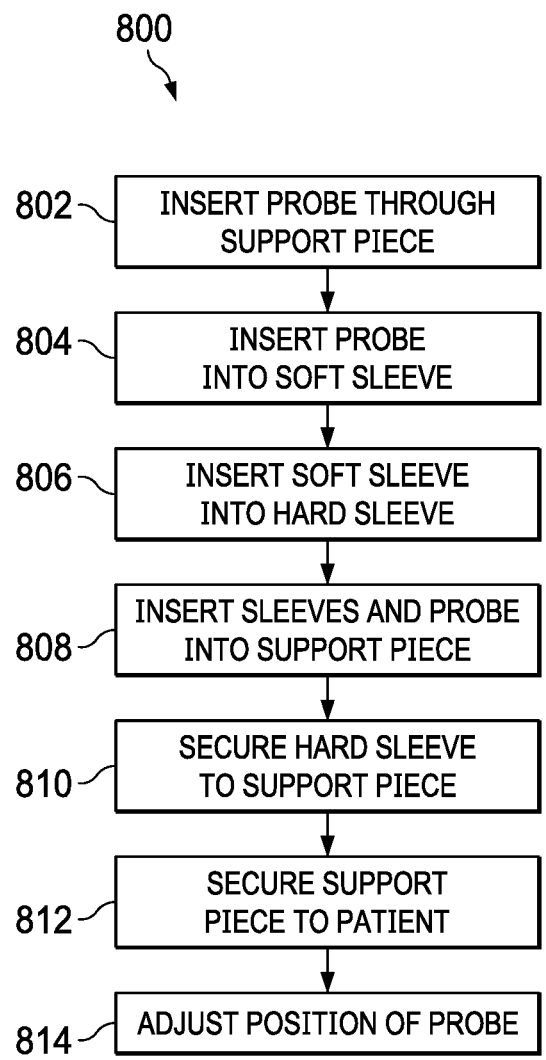
FIG. 8 is a flowchart of a method of securing an ultrasound transducer probe holder device to a patient, in accordance with an illustrative embodiment.

FIG. 8 is a flow chart of the steps 800 to secure ultrasound transducer probe holder 202 to a patient, in accordance with an illustrative embodiment. At 802, ultrasound transducer probe 204 is inserted through orifice 308 of support piece 302, through channel 309 of support piece 302, and out through bottom orifice 608 of channel 309. At 804, ultrasound transducer probe 204 is inserted into soft sleeve 402 by opening soft sleeve 402 at cut section 408. If hard sleeve 502 is to be used, at 806, soft sleeve 402 with ultrasound transducer probe 204 within, is inserted into hard sleeve 502. At 808, hard sleeve 502 and soft sleeve 402 with ultrasound transducer probe 204 within or just soft sleeve 402 with ultrasound transducer probe 204 within, are pulled up through bottom orifice 608 of channel 309 of support piece 302. At 810, hard sleeve 502 with soft sleeve 402 within (or just soft sleeve 402 if hard sleeve 502 is absent) is fixed relative to support piece 302 with an adjustment screw. The adjustment screw engaged with threaded hole 316 is tightened such that the adjustment screw abuts hard sleeve 502 (or soft sleeve 402 if hard sleeve 502 is not present). At 812, support piece 302 is secured to the appendage of a patient using the hook and loop fasteners though slots 322, 323. At 814, if needed, the position of ultrasound transducer probe 204 is adjusted. The flexibility of the shore A material comprising soft sleeve 402 allows positional adjustments. The adjustment screw may be loosened to make further positional adjustments.

The operations described above are not relegated to the order the operations were presented. Some operations can be performed prior to previously described operations and some can be performed simultaneously. The order the operations were presented does not imply an order for the operations to be performed in.

Figure 9:
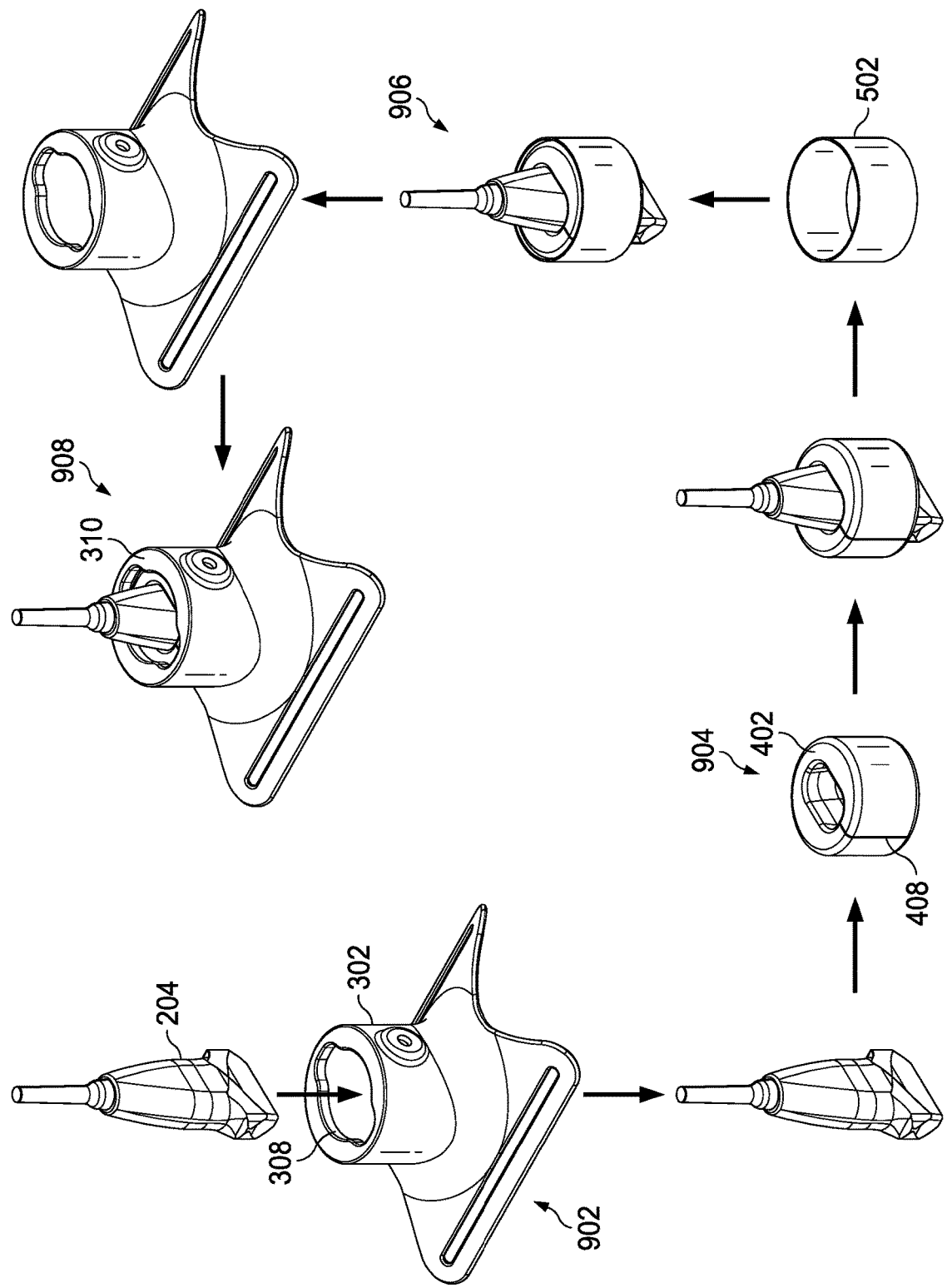
FIG. 9 illustrates a method of securing an ultrasound transducer probe holder in an ultrasound transducer probe holder device in accordance with an illustrative embodiment.

FIG. 9 illustrates a method of securing ultrasound transducer probe 204 in ultrasound transducer probe holder 202 in accordance with an illustrative embodiment. At 902, ultrasound transducer probe 204 is inserted through orifice 308 of support piece 302. At 904, ultrasound transducer probe 204 is inserted into soft sleeve 402 by opening soft sleeve 402 at cut section 408. This is possible because of the flexible shore A material of soft sleeve 402 is made out of. At 906, soft sleeve 402 with ultrasound transducer probe 204 within, is inserted into hard sleeve 502. At 908, hard sleeve 502 (with soft sleeve 402 within and with ultrasound transducer probe 204 within soft sleeve 402) is pulled up through bottom orifice 608 of channel 309 of support piece 302. Hard sleeve 502 and soft sleeve 402 may abut lip 310. Hard sleeve 502 with soft sleeve 402 is free to rotate within channel 309 of support piece 302. An adjustment screw threadably engaged with support piece 302 abuts hard sleeve 502 to fix hard sleeve 502 and soft sleeve 402 and ultrasound transducer probe 204 with respect to support piece 302 thus securing ultrasound transducer probe 204 in ultrasound transducer probe holder 202. When hard sleeve 502 is absent, the adjustment screw threadably engaged with support piece 302 abuts soft sleeve 402 to fix soft sleeve 402 and ultrasound transducer probe 204 with respect to support piece 302 thus securing ultrasound transducer probe 204 in ultrasound transducer probe holder 202.

Figure 10:
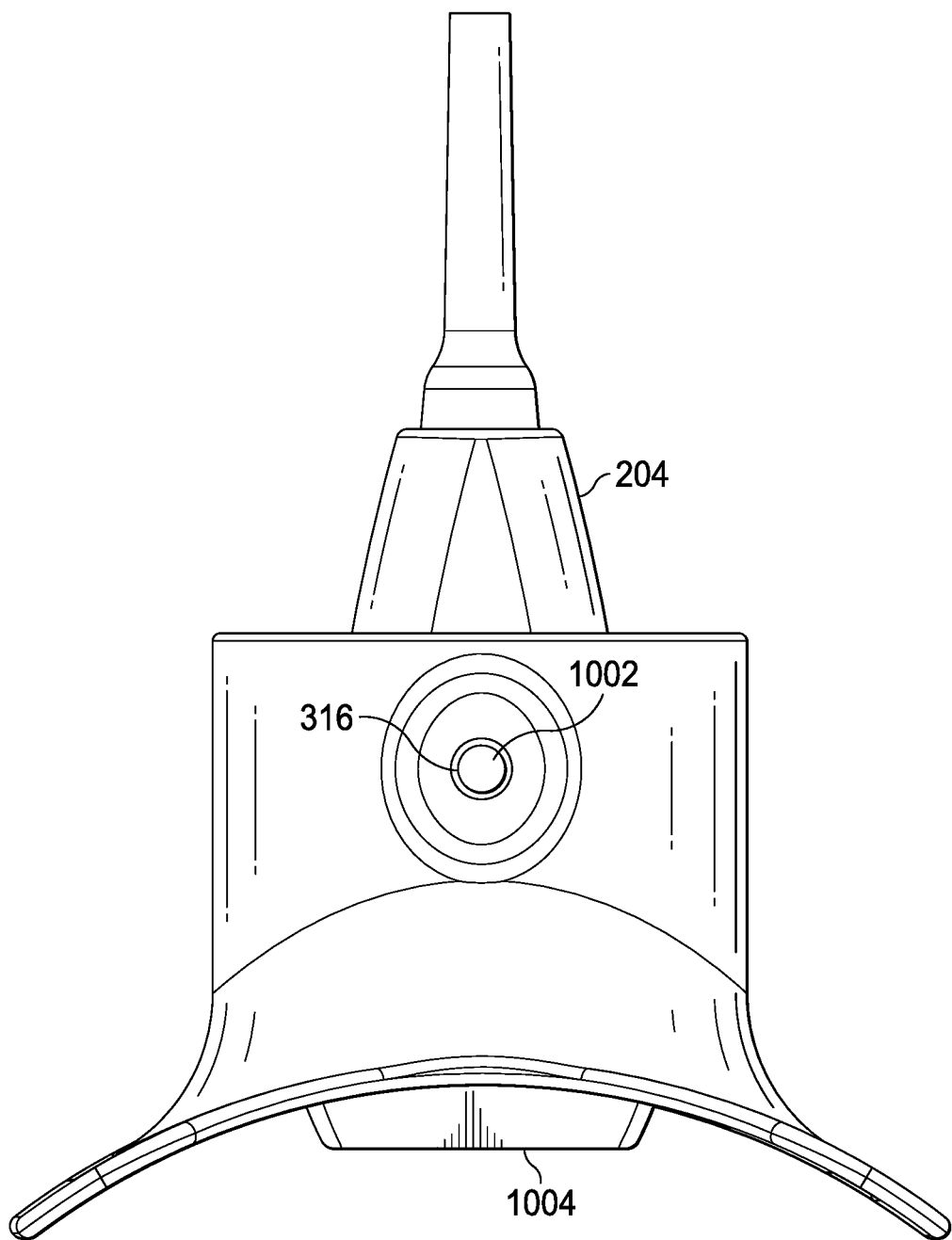
FIG. 10 illustrates an ultrasound transducer probe holder device in use, in accordance with an illustrative embodiment.

FIG. 10 illustrates an ultrasound transducer probe holder device in use, in accordance with an illustrative embodiment. Hard sleeve 502 is fixed relative to support piece 302 with adjustment screw 1002. Adjustment screw 1002, engaged with threaded hole 316, is tightened such that adjustment screw 1002 abuts hard sleeve 502. In the absence of hard sleeve 502, soft sleeve 402 is fixed relative to support piece 302 with adjustment screw 1002. Adjustment screw 1002, engaged with threaded hole 316, is tightened such that adjustment screw 1002 abuts soft sleeve 402. Support piece 302 is secured to the appendage of a patient using the hook and loop fasteners though slots 322, 323. Adjustment of the position of tip 1004 of ultrasound transducer probe 204 is such that tip 1004 is tightly touching patient appendage. Ultrasound transducer probe holder 202 ensures reduced movement of ultrasound transducer probe 204 during exercise movements which in turn provides for better visualization of blood flow than current FMD techniques.

Figure 11:
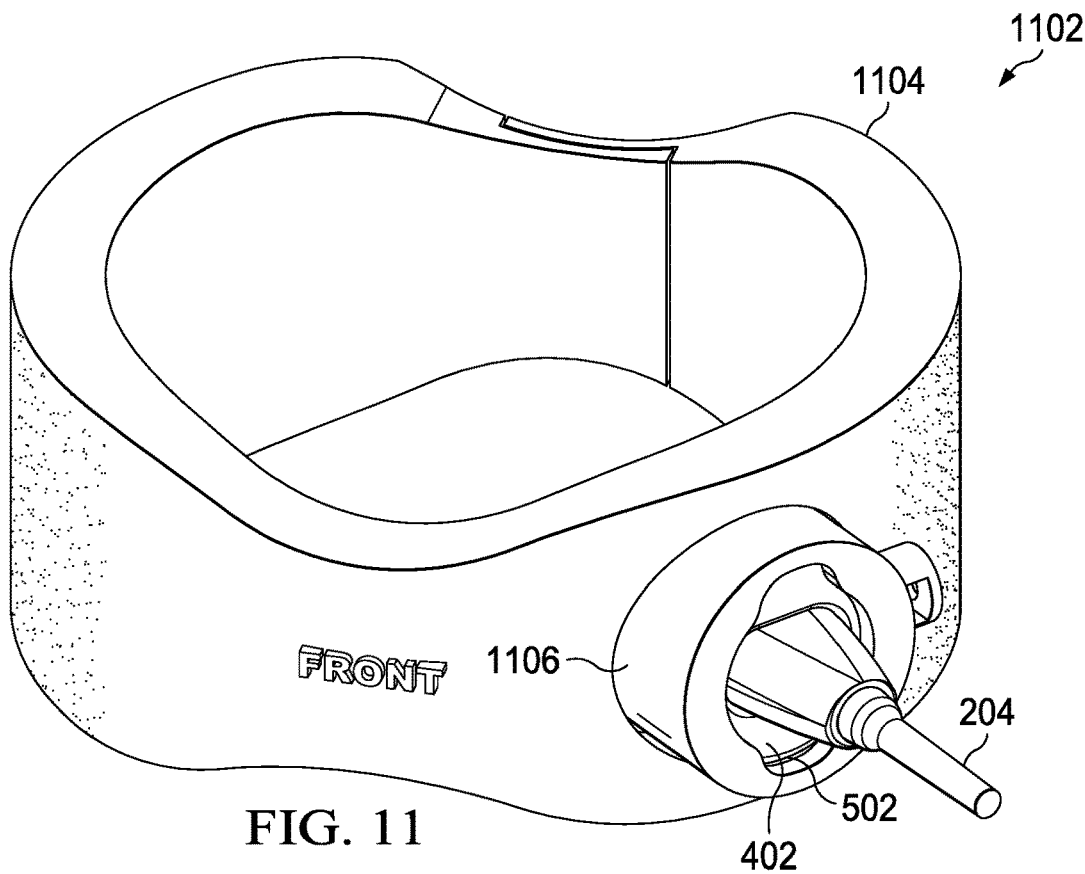
FIG. 11 illustrates an ultrasound transducer probe holder device in use, in accordance with an illustrative embodiment.

FIG. 11 illustrates an ultrasound transducer probe holder device with an ultrasound transducer probe, in accordance with an illustrative embodiment. Ultrasound transducer probe holder 1102 is an example of one implementation of ultrasound transducer probe holder 100 in FIG. 1. Ultrasound transducer probe holder 1102 may position ultrasound transducer probe 204 against the arm, leg, or neck of a patient to provide hands-free operation of FMD testing on a subject during exercise conditions. Ultrasound transducer probe holder 1102 may include brace 1104, support piece 1106, hard sleeve 502, and soft sleeve 402. The support piece and the hard sleeve may comprise a shore D material plastic, for example, polycarbonate material crafted with 3D printing. The soft sleeve may comprise a shore A material, for example, a silicone or urethane material and manufactured through room temperature vulcanization molding. The brace may comprise a soft foam material.

Figure 12:
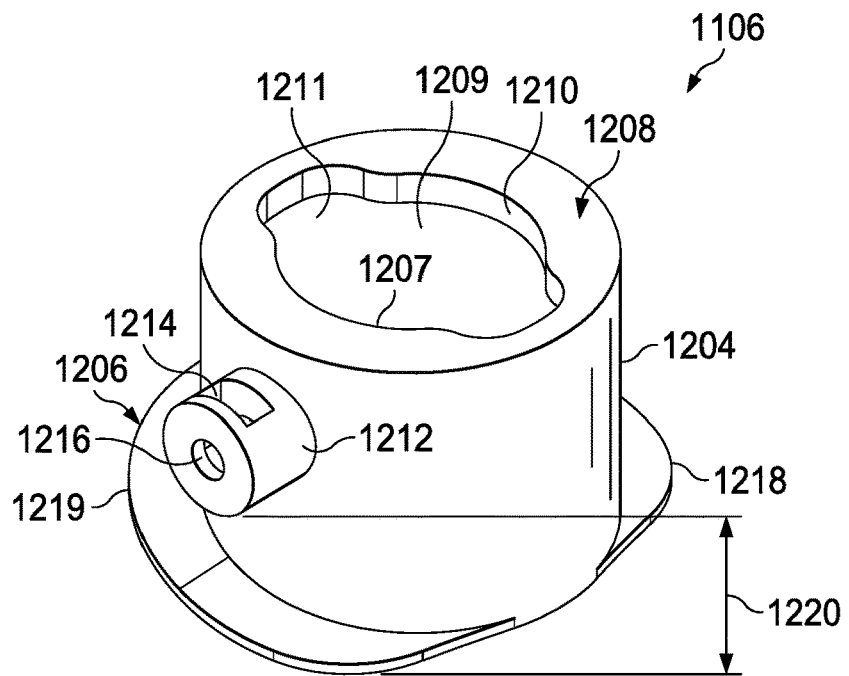
FIG. 12 illustrates a support piece, in accordance with an illustrative embodiment.

FIG. 12 illustrates support piece 1106 of ultrasound transducer probe holder 1102 in accordance with an illustrative embodiment. Support piece 1106 is an example of one implementation of support piece 102 in FIG. 1. Support piece 1106 may include trunk section 1204 and base 1206. Trunk section 1204 and base 1206 may be of unitary construction. Trunk section 1204 may be connected to base 1206.

Trunk section 1204 may include orifice 1208 leading to channel 1209. Channel 1209 extends through trunk section 1204 and base 1206. Channel 1209 may have cylindrical shape 1211. Channel 1209 may include orifice 1208 with a 2D shape 1207 of the transducer probe to allow probe insertion, and a bottom round orifice (shown as bottom orifice 1302 of FIG. 13) to allow insertion of the sleeves. Orifice 1208 of trunk section 1204 may include lip 1210. Lip 1210 may contact the hard sleeve (shown as hard sleeve 502 of FIG. 5) and the soft sleeve (shown as soft sleeve 402 of FIG. 4) when the sleeves are positioned within channel 1209 of support piece 1106 to prevent the sleeves from exiting the support piece 1106 through orifice 1208. Trunk section 1204 may include housing 1212. Housing 1212 may define cavity 1214 sized to accommodate a threaded nut. Housing 1212 may include hole 1216 sized to accommodate an adjustment screw. Hole 1216 may intersect cavity 1214 and lead to channel 1209. Hole 1216 may be a threaded hole which eliminates the need for a threaded nut within cavity 1214. An adjustment screw in hole 1216 may contact the hard sleeve when the hard and soft sleeves are both positioned within channel 1209 of support piece 1106. The adjustment screw is used to fix the position of the sleeves relative to support piece 1106. It is possible to operate ultrasound transducer probe holder 1102 with both the hard sleeve and the soft sleeve in conjunction within the support piece 1106. It is also possible to operate ultrasound transducer probe holder 1102 with the hard sleeve absent. When the hard sleeve is absent, the adjustment screw contacts the soft sleeve to secure the position of the soft sleeve relative to support piece 1106.

Base 1206 may include flanges 1218, 1219 extending from trunk section 1204. Flanges 1218, 1219 define space 1220 between flanges 1218, 1219 and housing 1212. Space 1220 is sized to accommodate the thickness of brace 1104. Brace 1104 is for securing ultrasound transducer probe holder 1102 to a patient. The flexibility of the material comprising brace 1104 allows for adjustment to accommodate various sizes of patient appendages.

Figure 13:
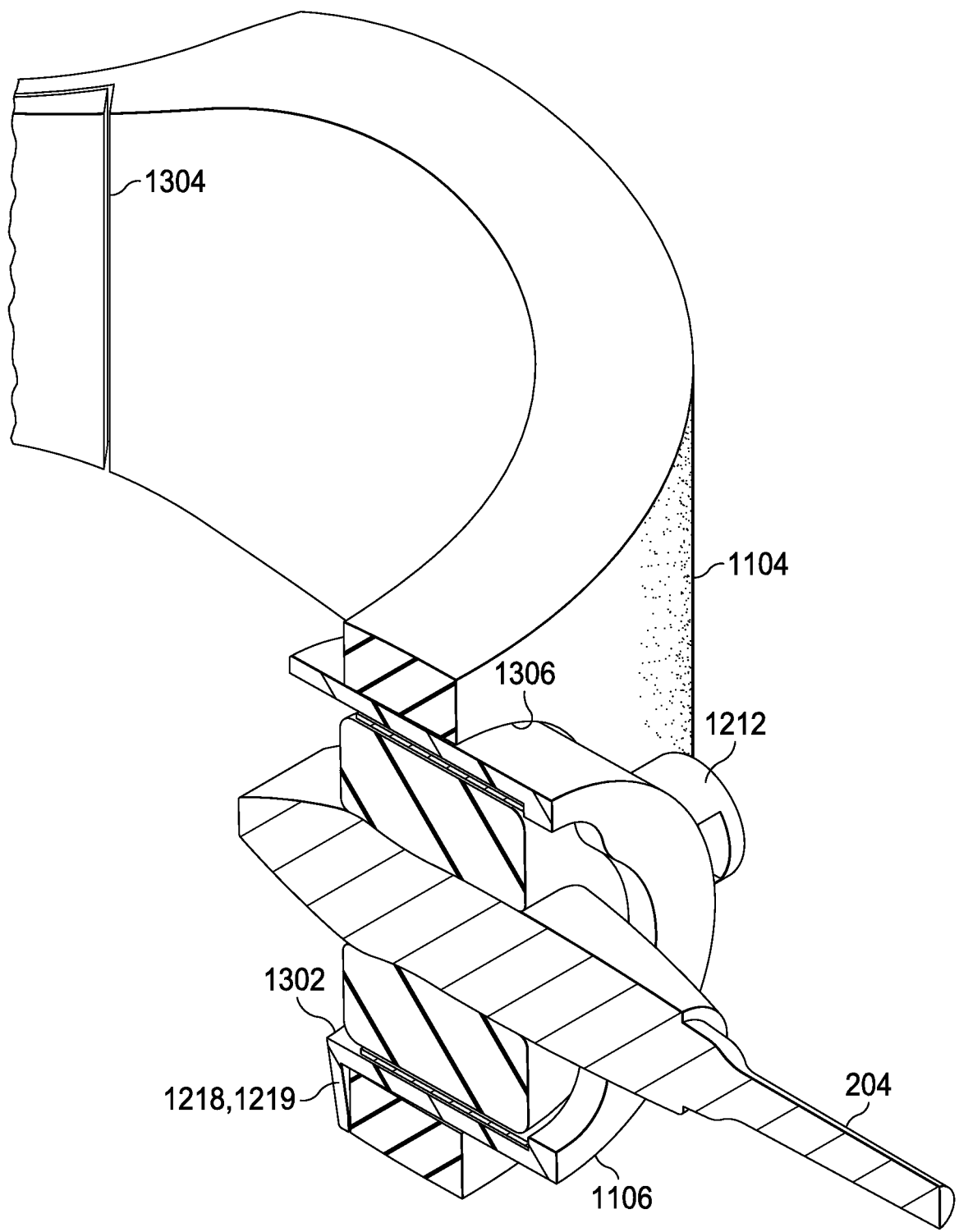
FIG. 13 illustrate an ultrasound transducer probe holder device in use in cross section, in accordance with an illustrative embodiment.

As best illustrated in FIG. 13, support piece 1106 is press fit within hole 1306 of brace 1104. Brace 1104, or rather the thickness thereof, fits in space 1220 defined between housing 1212 and flanges 1218, 1219 of support piece 1106. The soft material comprising brace 1104 allow hole 1306 to stretch and accommodate support piece 1106. Housing 1212 and flanges 1218, 1219 prevent support piece 1106 from inadvertent removal of support piece 1106 and ultrasound transducer probe 204 within from hole 1306 in brace 1104. Brace further includes cut line 1304 to allow brace 1104 to be place around an appendage of neck of a patient.

Outer shape 606 of hard sleeve 502 allows hard sleeve 502 to be inserted in to channel 309 through bottom orifice 1302 and rotate within channel 309 of support piece 1106. Bottom orifice 1302 is circular in shape. Outer shape 606 of hard sleeve 502 mimics the circular shape of bottom orifice 1302.

Figure 14:
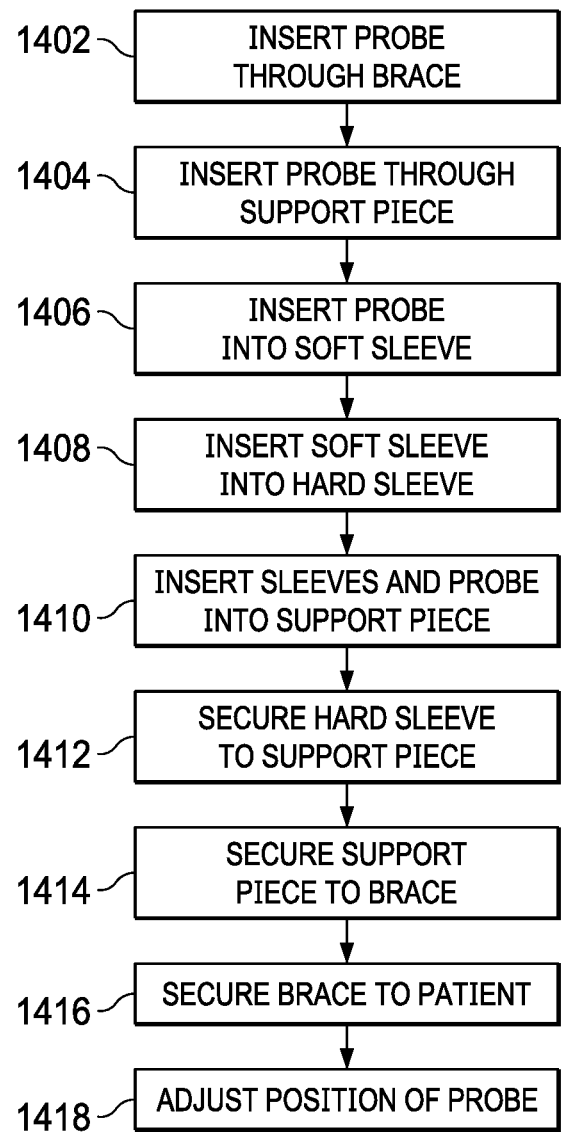
FIG. 14 is a flowchart of a method of securing an ultrasound transducer probe holder device to a patient, in accordance with an illustrative embodiment.

FIG. 14 is a flow chart of the steps 1400 to secure ultrasound transducer probe holder 1102 to a patient, in accordance with an illustrative embodiment. At 1402, ultrasound transducer probe 204 is passed through hole 1306 of brace 1104. At 1404 ultrasound transducer probe 204 is inserted through orifice 1208 of support piece 1106, through channel 1209 of support piece 1106, and out through bottom orifice 1302 of channel 1209. At 1406, ultrasound transducer probe 204 is inserted into soft sleeve 402 by opening soft sleeve 402 at cut section 408. If hard sleeve 502 is to be used, at 1408, soft sleeve 402 with ultrasound transducer probe 204 within, is inserted into hard sleeve 502. At 1410, hard sleeve 502 and soft sleeve 402 with ultrasound transducer probe 204 within or just soft sleeve 402 with ultrasound transducer probe 204 within, are pulled up through bottom orifice 1302 of channel 1209 of support piece 1106. At 1412, hard sleeve 502 with soft sleeve 402 within (or just soft sleeve 402 if hard sleeve 502 is absent) is fixed relative to support piece 1106 with an adjustment screw. The adjustment screw engaged with hole 1216 is tightened such that the adjustment screw abuts hard sleeve 502 (or soft sleeve 402 if hard sleeve 502 is not present). At 1414, support piece 1106 with the transducer probe securely held within is secured with a friction fit in hole 1306 of brace 1104.

Support piece 1106 is passed through hole 1306 such that housing 1212 is adjacent an outside surface of brace 1104 while flanges 1218, 1219 abut an inside surface of brace 1104. Space 1220 is sized to accept the thickness of brace 1104. The soft material of brace 1104 allow hole 1306 to stretch such that brace 1104 grips support piece 1106. At 1416, brace 1104 with support piece 1106 securely held within is secured to the appendage of a patient by opening brace 1104 at cut line 1304 and wrapping brace 1104 around an appendage of a patient. At 1418, if needed, the position of ultrasound transducer probe 204 is adjusted. The flexibility of the shore A material comprising soft sleeve 402 allows positional adjustments. The adjustment screw may be loosened to make further positional adjustments.

Figure 15:
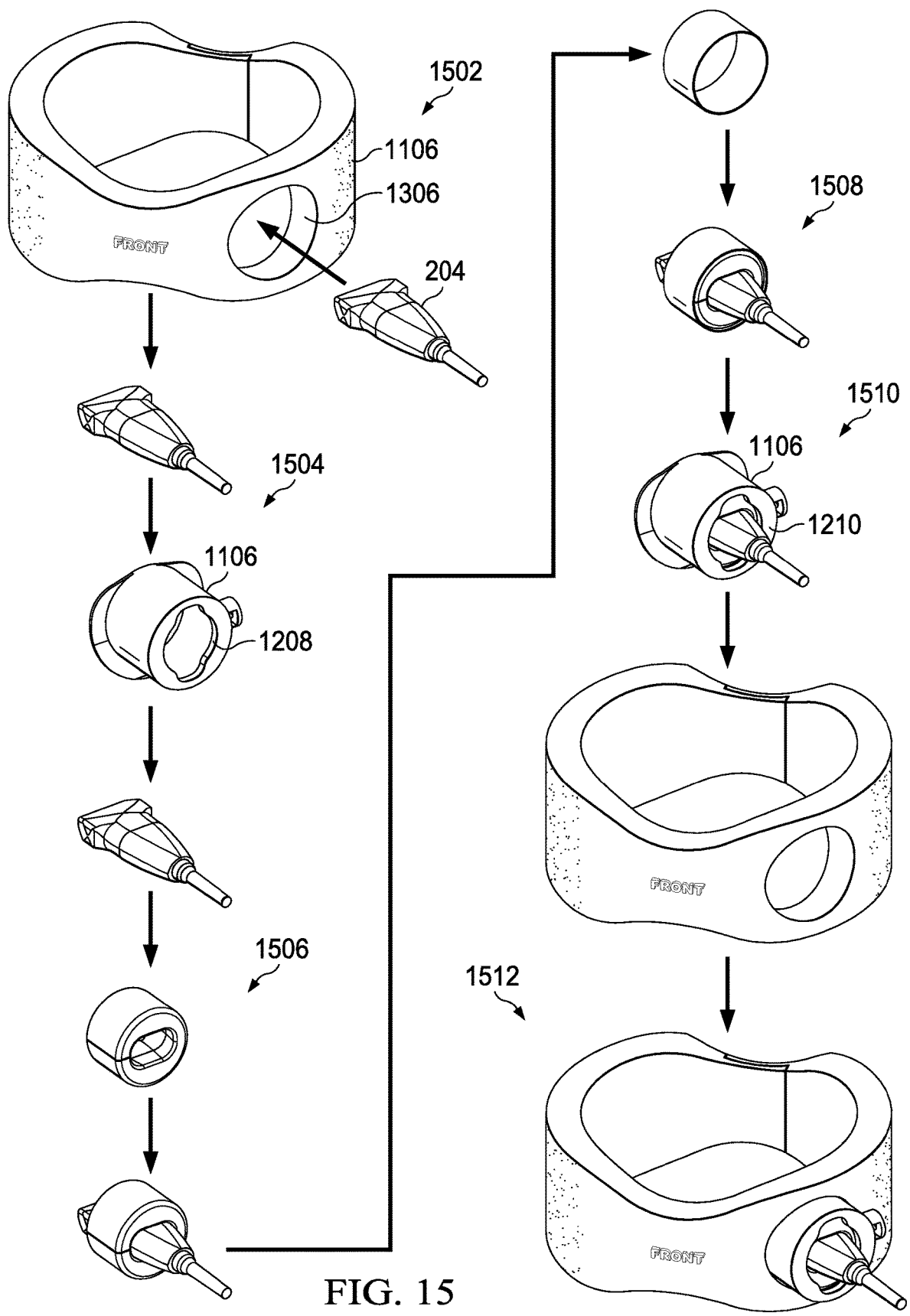
FIG. 15 illustrates a method of securing an ultrasound transducer probe holder in an ultrasound transducer probe holder device in accordance with an illustrative embodiment.

FIG. 15 illustrates a method of securing ultrasound transducer probe 204 in ultrasound transducer probe holder 1102 in accordance with an illustrative embodiment. At 1502 ultrasound transducer probe 204 is inserted through hole 1306 of brace 1104. At 1504, ultrasound transducer probe 204 is inserted through orifice 1208 of support piece 1106. At 1506, ultrasound transducer probe 204 is inserted into soft sleeve 402 by opening soft sleeve 402 at cut section 408. This is possible because of the flexible shore A material of soft sleeve 402 is made out of. At 1508, soft sleeve 402 with ultrasound transducer probe 204 within, is inserted into hard sleeve 502. At 1510, hard sleeve 502 (with soft sleeve 402 within and with ultrasound transducer probe 204 within soft sleeve 402) is pulled up through bottom orifice 1302 of channel 1209 of support piece 1106. Hard sleeve 502 and soft sleeve 402 may abut lip 1210. Hard sleeve 502 with soft sleeve 402 is free to rotate within channel 1209 of support piece 1106. An adjustment screw threadably engaged with support piece 1106 abuts hard sleeve 502 to fix hard sleeve 502 and soft sleeve 402 and ultrasound transducer probe 204 with respect to support piece 1106 thus securing ultrasound transducer probe 204 in ultrasound transducer probe holder 1102. When hard sleeve 502 is absent, the adjustment screw threadably engaged with support piece 1106 abuts soft sleeve 402 to fix soft sleeve 402 and ultrasound transducer probe 204 with respect to support piece 1106 thus securing ultrasound transducer probe 204 in ultrasound transducer probe holder 202. At 1512, support piece 1106 with ultrasound transducer probe 204 secured within is pulled into and secured within hole 1306 of brace 1104.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An ultrasound transducer probe holder device, comprising:
    a trunk section with an orifice formed at a first end of the trunk section, the orifice in communication with a channel within the trunk section, wherein the orifice forms a lip at the first end of the trunk section;
    a base unitarily formed with the trunk section, the base formed at a second end of the trunk section opposite the first end of the trunk section;
    a sleeve removably located within the channel, wherein the sleeve abuts the lip such that the sleeve is retained within the trunk section; and
    an adjustment screw fitted in the trunk section, wherein the adjustment screw is movable into the channel and abuts the sleeve to secure the sleeve to the trunk section.

2. The ultrasound transducer probe holder device of claim 1, wherein the channel has a cylindrical shape.

3. The ultrasound transducer probe holder device of claim 1, wherein the channel has a cylindrical shape and the sleeve has a round outer shape that matches the cylindrical shape of the channel such that the sleeve is receivable into the channel.

4. The ultrasound transducer probe holder device of claim 1, wherein the orifice has a 2D shape such that an ultrasound transducer probe is insertable through the orifice in communication with the channel.

5. The ultrasound transducer probe holder device of claim 1, wherein the base includes flanges extending from the second end of the trunk section and the flanges form a curved surface.

6. The ultrasound transducer probe holder device of claim 1, further comprising a threaded hole in the trunk section engaged with the adjustment screw where the threaded hole leads to the channel.

7. The ultrasound transducer probe holder device of claim 1, further comprising slots in the base for accommodating fastener straps.

8. The ultrasound transducer probe holder device of claim 1, wherein the sleeve has a holding section with a shape such that an ultrasound transducer probe is receivable within the holding section.

9. The ultrasound transducer probe holder device of claim 1, wherein the sleeve further comprises:
    a holding section such that a transducer probe is insertable within the holding section; and
    a cut section in the holding section such that the sleeve is openable to accommodate the transducer probe within the holding section.

10. The ultrasound transducer probe holder device of claim 1, wherein the channel has a cylindrical shape and the sleeve has a round outer shape sized to the cylindrical shape, wherein the sleeve is rotatable with respect to the trunk section within the channel.

11. The ultrasound transducer probe holder device of claim 1, wherein the sleeve comprises a soft sleeve positioned within a hard sleeve and the adjustment screw abuts the hard sleeve.

12. The ultrasound transducer probe holder device of claim 1, wherein the sleeve comprises a soft sleeve and a hard sleeve and wherein the channel has a cylindrical shape and the hard sleeve has a round outer shape sized to the cylindrical shape, wherein the hard sleeve and the soft sleeve are rotatable together with respect to the trunk section within the channel.

13. The ultrasound transducer probe holder device of claim 1, further comprising a flexible brace having a hole, wherein the trunk section extends through the hole and the base includes flanges configured to abut an inside surface of the flexible brace.

14. A method of securing an ultrasound transducer probe holder device to a patient, comprising:
    inserting an ultrasound transducer probe through an orifice in communication with a channel within a support piece, wherein the support piece includes a trunk section unitarily formed with a base, the orifice formed at a first end of the trunk section wherein the orifice forms a lip at the first end of the trunk section, and wherein the base is formed at a second end of the trunk section opposite the first end of the trunk section;

inserting the ultrasound transducer probe into a sleeve;

inserting the sleeve with the ultrasound transducer probe into the support piece, wherein the sleeve abuts the lip such that the sleeve is retained within the trunk section of the support piece;

securing the sleeve to the support piece with an adjustment screw fitted in the trunk section where the adjustment screw abuts the sleeve; and securing the support piece to the patient.

15. The method of claim 14, further comprising adjusting a position of the ultrasound transducer probe relative to the patient.

16. The method of claim 14, wherein securing the sleeve to the support piece includes rotating the adjustment screw housed in the trunk section of the support piece.

17. The method of claim 14, wherein securing the support piece to the patient includes accommodating fastener straps through slots in the base of the support piece.

18. The method of claim 14, wherein securing the support piece to the patient includes securing the support piece in a hole of a brace and securing the brace to the patient.

19. The method of claim 14, further comprising adjusting a position of a tip of the ultrasound transducer probe while within the sleeve such that the tip is contacting the patient.

20. The method of claim 14, wherein the sleeve comprises a soft sleeve positioned within a hard sleeve and the adjustment screw abuts the hard sleeve.

* * * * *